US009254215B2

(12) United States Patent
Mueller

(10) Patent No.: US 9,254,215 B2
(45) Date of Patent: *Feb. 9, 2016

(54) KNEE BRACE

(71) Applicant: Mueller Sports Medicine, Inc., Prairie du Sac, WI (US)

(72) Inventor: Brett Mueller, Middleton, WI (US)

(73) Assignee: Mueller Sports Medicine, Inc., Prairie du Sac, WI (US)

( * ) Notice: Subject to any disclaimer, the term of this patent is extended or adjusted under 35 U.S.C. 154(b) by 205 days.

This patent is subject to a terminal disclaimer.

(21) Appl. No.: 14/192,713

(22) Filed: Feb. 27, 2014

(65) Prior Publication Data

US 2014/0243722 A1 Aug. 28, 2014

Related U.S. Application Data

(60) Provisional application No. 61/770,926, filed on Feb. 28, 2013, provisional application No. 61/771,228, filed on Mar. 1, 2013.

(51) Int. Cl.
*A61F 5/00* (2006.01)
*A61F 5/01* (2006.01)

(52) U.S. Cl.
CPC .................................. *A61F 5/0109* (2013.01)

(58) Field of Classification Search
CPC ... A61F 5/0109; A61F 5/0104; A61F 5/0123; A61F 5/0102; A61F 2005/0139; A61F 2005/0137; A61F 2005/0174; A61F 2005/0181; A61F 5/0125; A61F 5/0106; A61F 2005/0179; A61F 5/01; A61F 2005/0172; A61F 5/0118; A61F 5/02; A41D 13/0153; A41D 13/0562; A41D 13/0568; A41D 13/065; A63B 2071/125; A63B 2209/10; A63B 2243/0025; A63B 2243/0095; A63B 71/1225; G08G 1/0955
USPC .................................. 602/16, 23–28; 128/882
See application file for complete search history.

(56) References Cited

U.S. PATENT DOCUMENTS

| 3,046,981 | A | * | 7/1962 | Biggs, Jr. | A61F 5/0109 602/26 |
| 5,024,216 | A | * | 6/1991 | Shiono | A61F 5/0123 2/24 |
| 5,472,413 | A | * | 12/1995 | Detty | A61F 5/0104 2/16 |
| 7,749,183 | B2 | | 7/2010 | Ingimundarson | |
| 7,959,590 | B2 | | 6/2011 | Scott | |
| 2009/0156973 | A1 | * | 6/2009 | Scott | A61F 5/0106 602/26 |

* cited by examiner

*Primary Examiner* — Michael Brown
(74) *Attorney, Agent, or Firm* — Rick L. Abegglen

(57) ABSTRACT

A knee brace for use by athletes or others requiring protection and support of the knee. The knee brace includes a base and a spider member. The base is comprised of elastic material and configured to closely fit around portions of the knee and adjacent leg portions. A spider member having upper and lower pairs of tensioning straps is fastened to the interior surface of the base, with the tensioning straps extending through upper and lower apertures in the base for detachable attachment to the exterior surface of the base.

5 Claims, 8 Drawing Sheets

KNEE BRACE

CROSS REFERENCE TO RELATED APPLICATIONS

This application claims priority to provisional application No. 61/770,926 filed Feb. 28, 2013, the disclosure of which is incorporated by reference. This application claims priority to provisional application No. 61/771,228 filed Mar. 1, 2013, the disclosure of which is incorporated by reference.

FIELD OF THE INVENTION

This invention relates generally to the field of articles worn by persons to reduce the likelihood, severity, or exacerbation of injury to the body, and more specifically to the field of braces worn on the knee.

BACKGROUND OF THE INVENTION

Flexible knee braces are used by athletes and other persons engaged in vigorous physical activity to protect the knee from injury and to avoid exacerbation of existing injury. The knee is one of the most heavily used joints of the body, as it is used in any activity that involves walking or running. The knee is also a common subject of injury, due to the relatively high levels of stress it must bear. During normal ambulation, in occupations involving physical labor, and especially during strenuous sports, the knee can undergo abnormal motions as a result of quick changes in direction, fatigue, uneven surfaces, or impacts. These abnormal motions can cause sprains or more serious injuries, including dislocation, stretching, or tearing of the tissues that make up the knee.

Several different types of abnormal motion can cause injury to the knee. First, hyperextension of the knee joint can occur, wherein the knee flexes in its normal front to back fashion but beyond its normal range of motion. A second type of abnormal motion is axial rotation, wherein the lower leg is twisted rotationally relative to the thigh about the knee joint. A third type of abnormal motion is lateral flexure of the lower leg relative to the thigh, wherein the knee joint flexes from side to side instead of the normal front to back motion. In addition, abnormal motion of the patella (kneecap) can result in injuries such as chondromalacia patella, which is a softening or degeneration of the undersurface of the patella, and dislocation of the patella, also known as subluxation of the patella.

Devices to protect the knee against abnormal motions have been used for many years, in a variety of specific embodiments which vary in their abilities to protect against the different types of abnormal motions. Besides protecting the knee against abnormal motions, the devices sometimes provide additional benefits such as insulating the knee to keep it warm, protecting the knee against impact, or compressing the knee to reduce discomfort. However, the protections afforded by these devices against abnormal motion are often accompanied by a reduction in range or ease of normal motion. These devices can also have other undesirable aspects such as added weight on the leg, potential for self-injury or injury to others caused by rigid components, difficulty of application and removal, cost, appearance, and irritation or chafing of the skin.

For these reasons, there has long been motivation to find an improved knee brace which can protect the knee from abnormal motions without affecting the range or ease of normal motion, while avoiding the undesirable aspects of prior art devices.

SUMMARY OF THE INVENTION

In a preferred embodiment, a knee brace according to the present invention includes a base and a spider member having pairs of upper and lower tensioning straps, wherein the spider member is permanently fastened to the interior surface of the base.

According to another aspect of the invention, a knee brace according to the present invention includes a base and a spider member having pairs of upper and lower tensioning straps, wherein the spider member is permanently fastened to the base by a plurality of stitches through the mid-line axes of the base and spider member.

According to another aspect of the invention, a knee brace according to the present invention includes a base with pairs of upper and lower apertures, and a spider member positioned between the base and the leg of the person when worn and having pairs of upper and lower tensioning straps, wherein the tensioning straps extend through the apertures in the base when the brace is worn.

Further objects, features, and advantages of the invention will be apparent from the following detailed description when taken in conjunction with the accompanying drawings.

DETAILED DESCRIPTION OF THE INVENTION

Figure 1A:
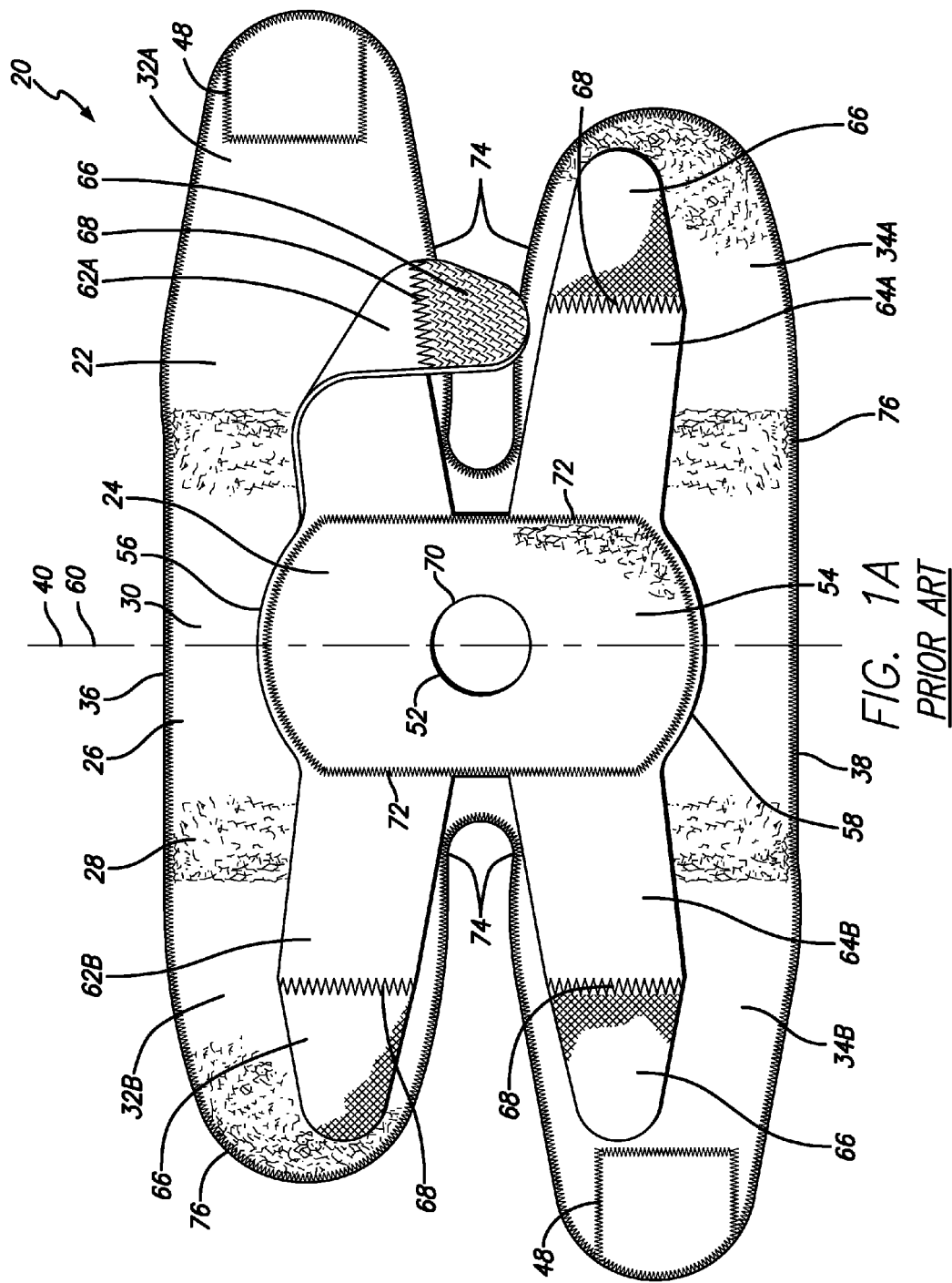
FIG. 1A is a plan view of a prior art knee brace, laid flat to expose the exterior surface of the brace.
Figure 1B:
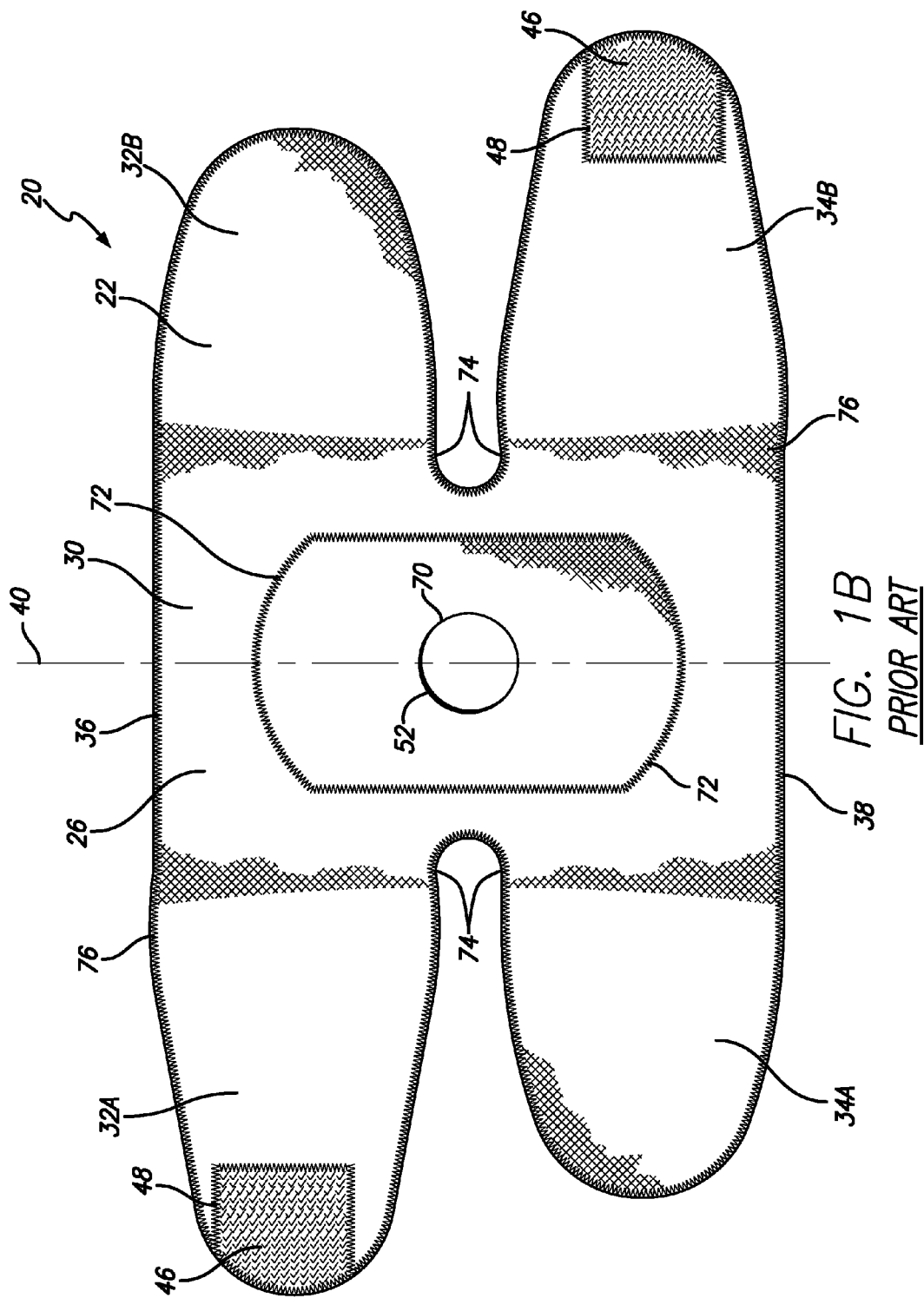
FIG. 1B is a plan view of the prior art knee brace of FIG. 1A, laid flat to expose the interior surface of the brace.

Referring to the drawings, FIGS. 1A and 1B show a prior art knee brace 20, similar to the design taught in U.S. Pat. No. 5,472,413, the contents of which are hereby incorporated by reference. The prior art knee brace 20 includes a base member 22 and a spider member 24, each made by cutting planar sheets 26 of an elastomeric material into the desired shapes. The exterior surface 31 of the base member 22 is preferably covered with fabric bearing fiber loops 28 that adheres to hook-type material when the fiber loops and hook-type material are pressed together.

The base 22 of the prior art knee brace 20 has a base central portion 30 extending vertically from an upper edge 36 to a lower edge 38, and has a mid-line axis 40 running vertically down the middle of base central portion 30. The base 22 includes a first upper mounting strap 32A, a second upper mounting strap 32B, a first lower mounting strap 34A, and a base second lower mounting strap 34B extending from the central portion 30.

As perhaps best shown in FIG. 1B which shows the interior surface 39 of the base 22, the first upper mounting strap 32A and first lower mounting strap 34A terminate in hook-type strap fastening tabs 46 suitable for detachable attachment to the fabric bearing fiber loops 28 on the exterior surface 31 of the base member 22. The strap fastening tabs 46 are sewn to the mounting straps with stitches 48.

The base also has a kneecap opening 52 to receive the kneecap when the brace is worn, it may be formed to include a recess 74 to prevent bunching when the brace is worn, and the base preferably includes edge binding 76, although none of these features are required.

As perhaps best shown in FIG. 1A which shows the exterior surface 31 of the base 22, the prior art knee brace 20 includes a spider member 24. The spider member 24 has a spider member central portion 54 extending vertically from an upper edge 56 to a lower edge 58, and has a mid-line axis 60 running vertically down the middle of the spider member central portion 54. The spider member 24 is permanently attached to the exterior surface 31 of the base 22 by stitches 72 that extend around the periphery of the spider member central portion 54.

The spider member 24 includes a first upper tensioning strap 62A, a second upper tensioning strap 62B, a first lower tensioning strap 64A, and a second lower tensioning strap 64B extending from the central portion 54. Each of the tensioning straps 62A, 62B, 64A, 64B terminates in hook-type fastening tabs 66 suitable for detachable attachment to the fabric 28 on the exterior surface of the base 22 and sewn to the tensioning straps with stitches 68. The spider member 24 also has a kneecap opening 70 to receive the kneecap when the brace is worn.

Figure 2A:
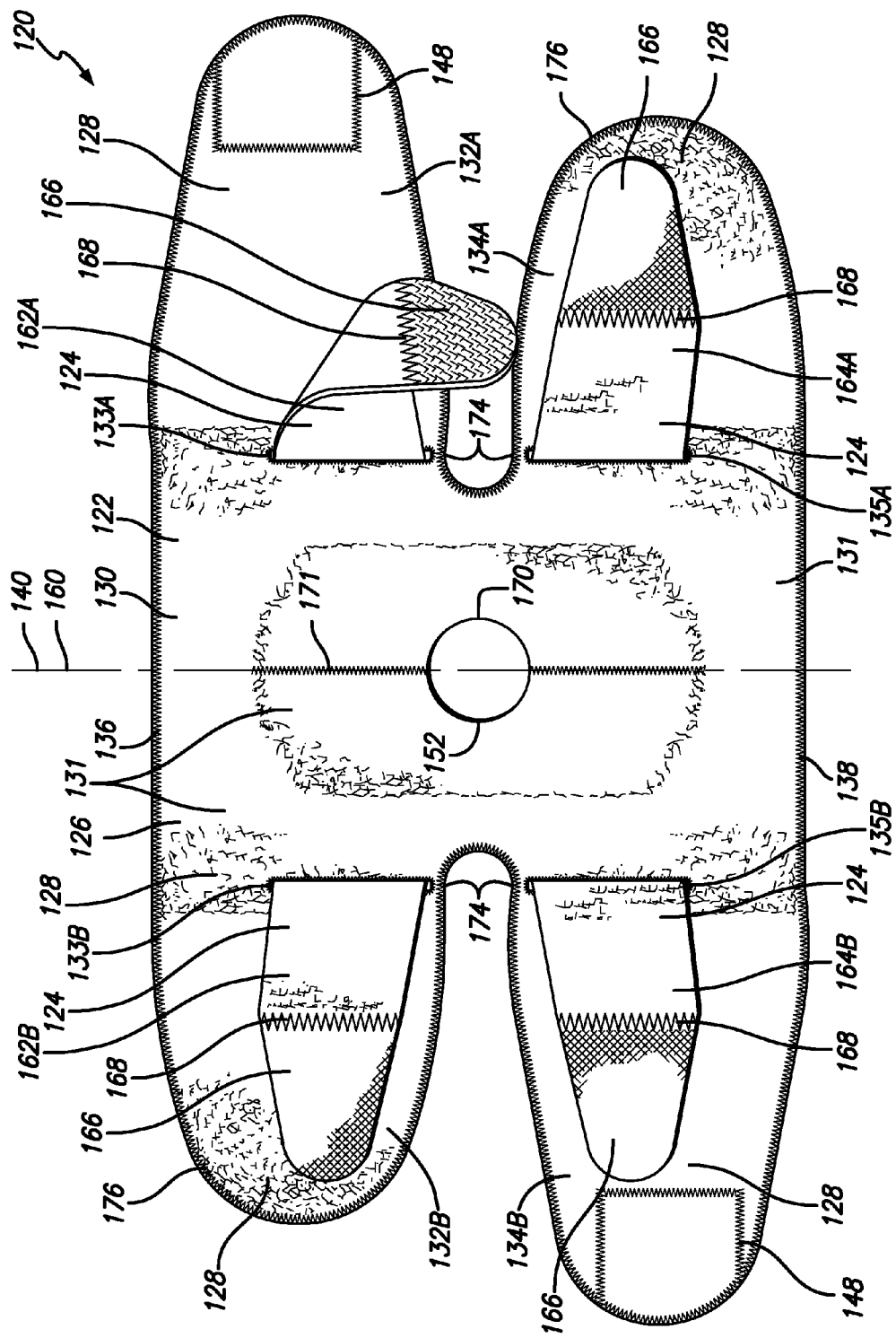
FIG. 2A is a plan view of a knee brace according to the present invention, laid flat to expose the exterior surface of the brace.
Figure 2B:
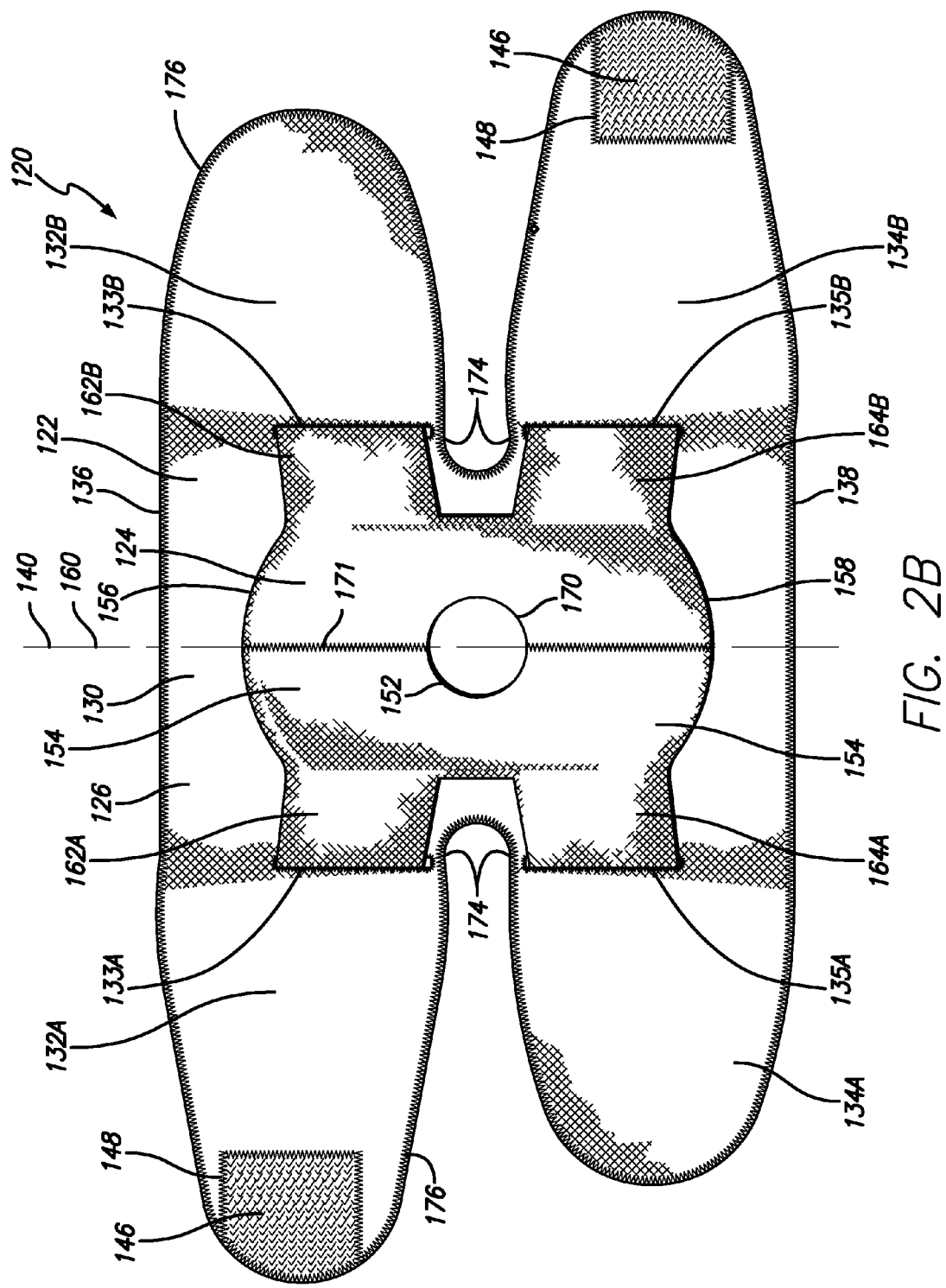
FIG. 2B is a plan view of the knee brace of FIG. 2A, laid flat to expose the interior surface of the brace.
Figure 3A:
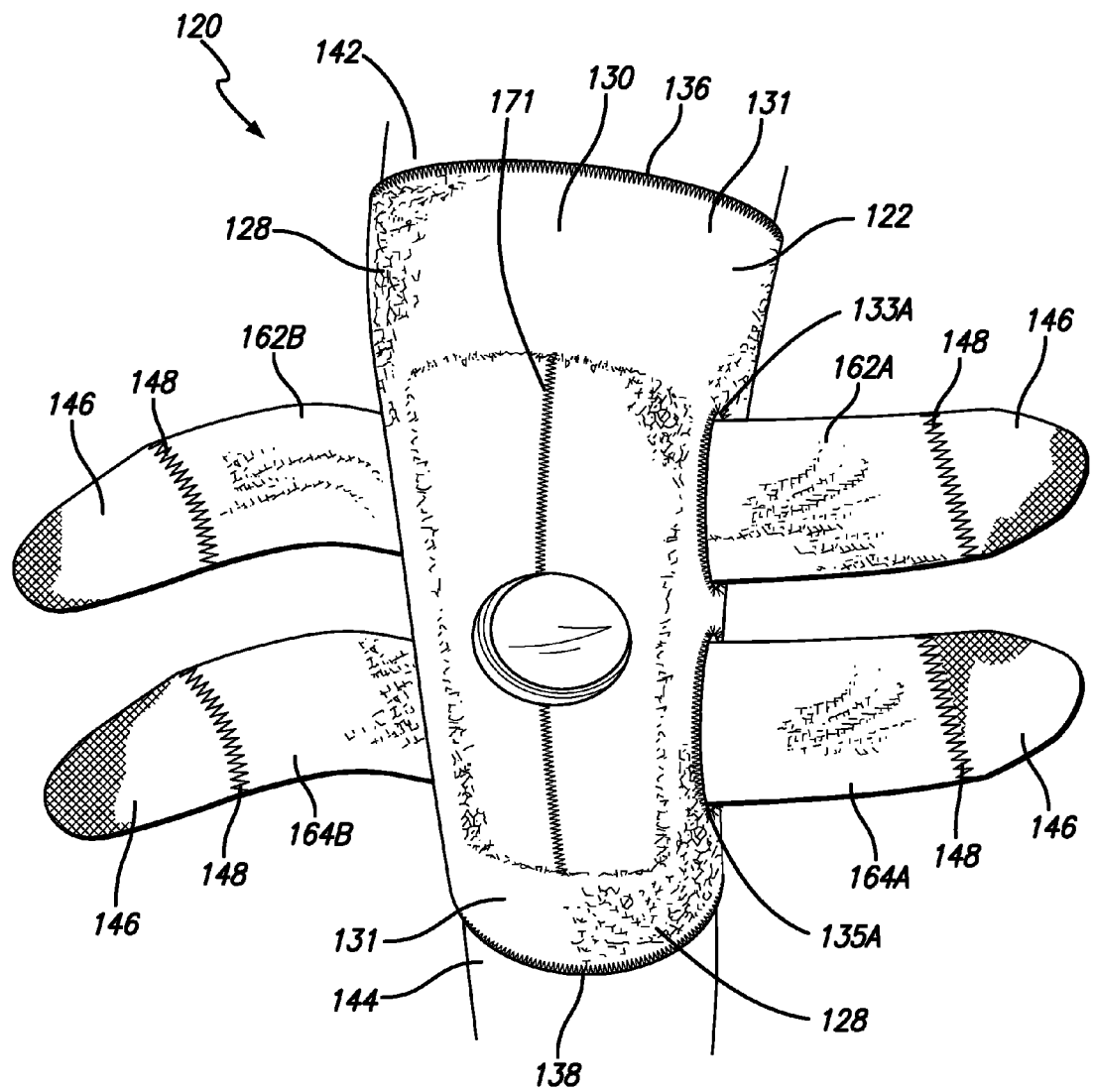
FIG. 3A is a front view of the knee brace of FIGS. 2A-2B, applied to the leg of a person with the base mounting straps fastened, but with the spider straps unfastened.
Figure 3B:
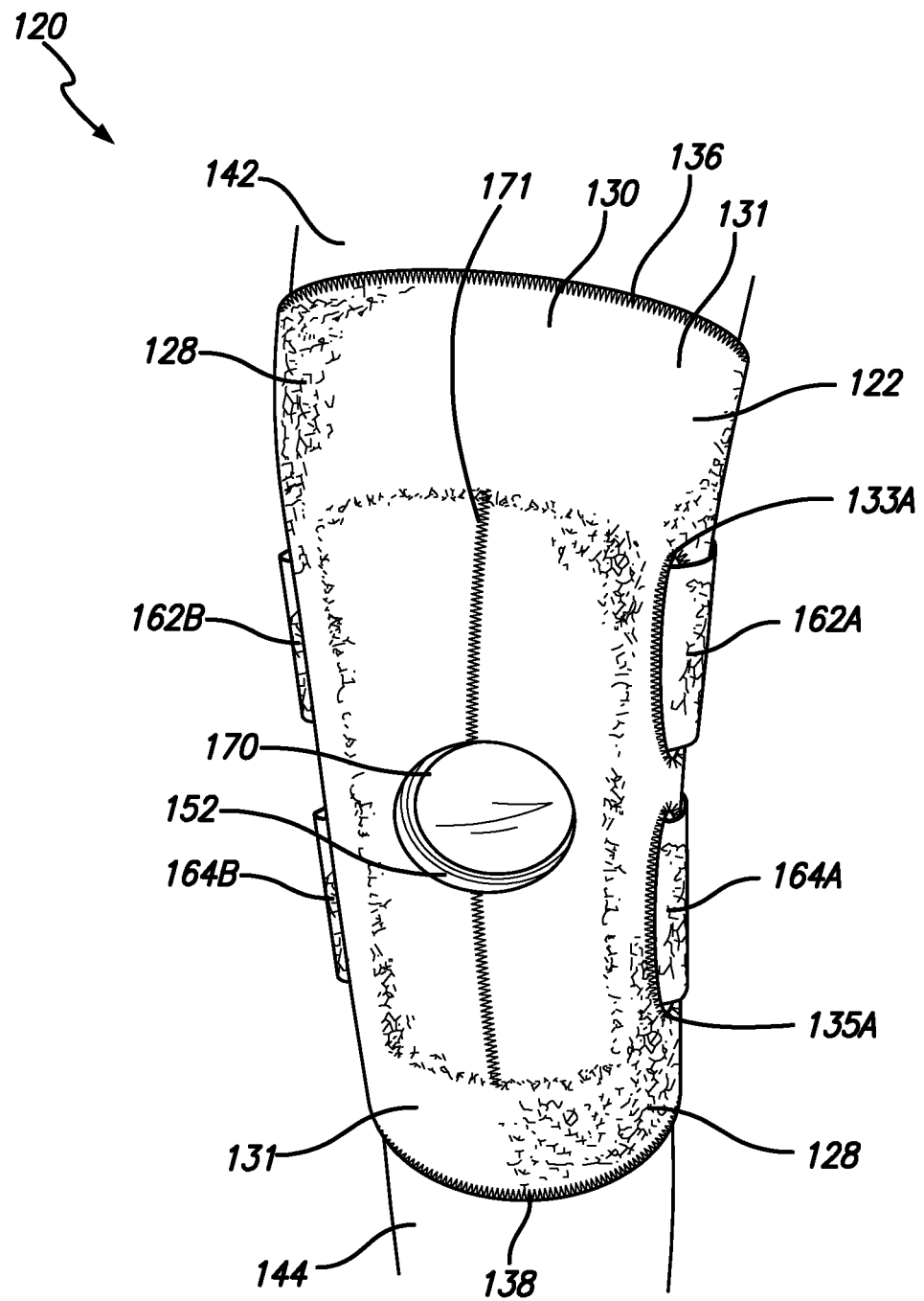
FIG. 3B is a front view of the knee brace of FIGS. 2A-2B, applied to the leg of a person with the base mounting straps fastened, and with the spider straps fastened as well.

FIGS. 2A and 2B show exterior and interior plan views, respectively, of a knee brace 120 according to the present invention laid flat. The knee brace 120 includes a base member 122 and a spider member 124, each made by cutting planar sheets 126 of an elastomeric material into the desired shapes. The outer surface of the base member 122 is preferably covered with fabric bearing fiber loops 128 that adheres to hook-type material when the fiber loops and hook-type material are pressed together.

The base 122 of the knee brace 120 has a base central portion 130 extending vertically from an upper edge 136 to a lower edge 138, and has a mid-line axis 140 running vertically down the middle of base central portion 130. The base 122 includes a first upper mounting strap 132A, a second upper mounting strap 132B, a first lower mounting strap 134A, and a base second lower mounting strap 134B extending from the central portion 130.

As perhaps best shown in FIG. 2B which shows the interior surface 139 of the base 122, the first upper mounting strap 132A and first lower mounting strap 134A terminate in hook-type strap fastening tabs 146 suitable for detachable attachment to the fabric bearing fiber loops 128 on the external surface 131 of the base 122. The hook-type strap fastening tabs 146 are sewn to the mounting straps with stitches 148.

Figure 4A:
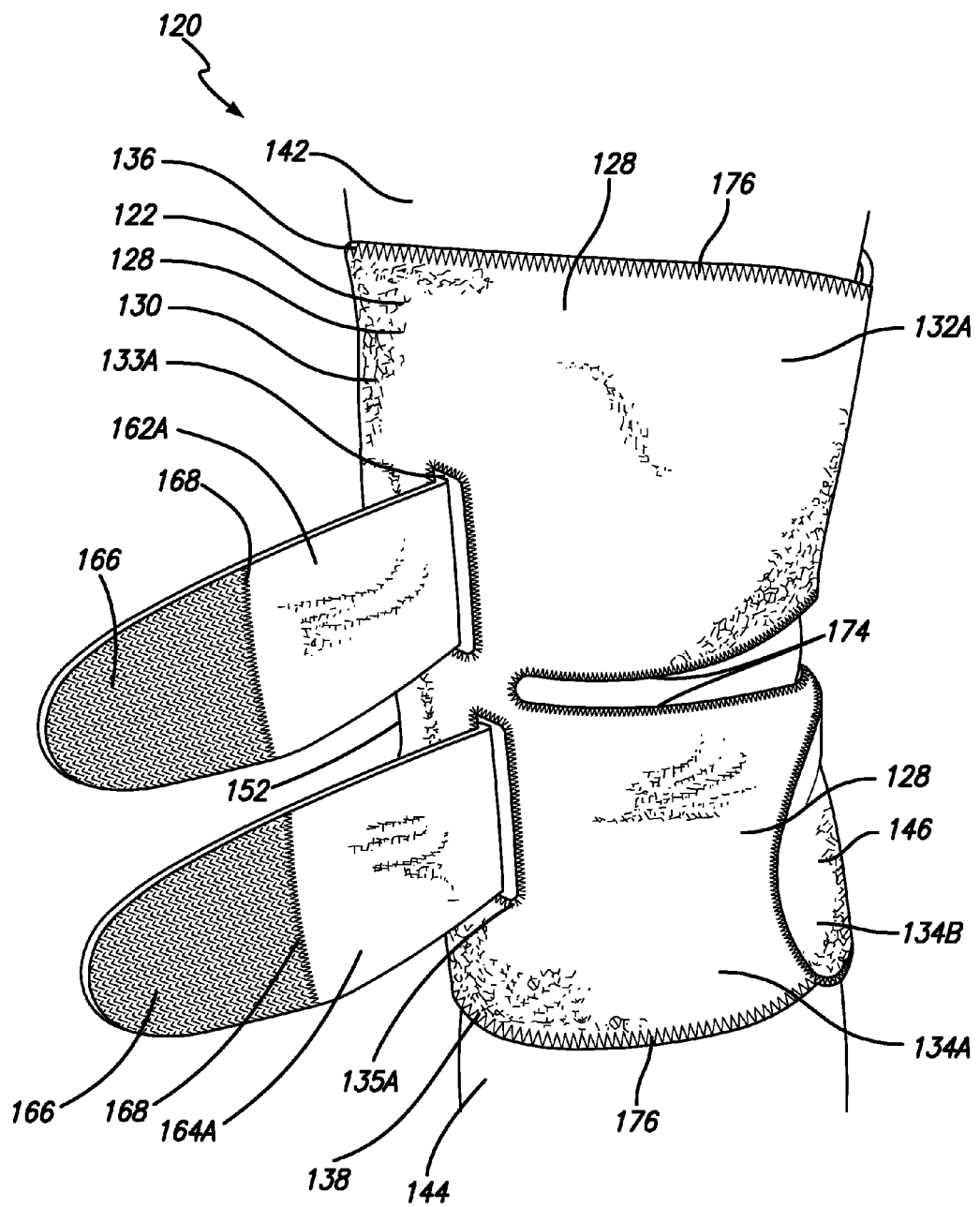
FIG. 4A is a side view of the knee brace of FIGS. 2A-2B, applied to the leg of a person with the base mounting straps fastened, but with the spider straps unfastened.
Figure 4B:
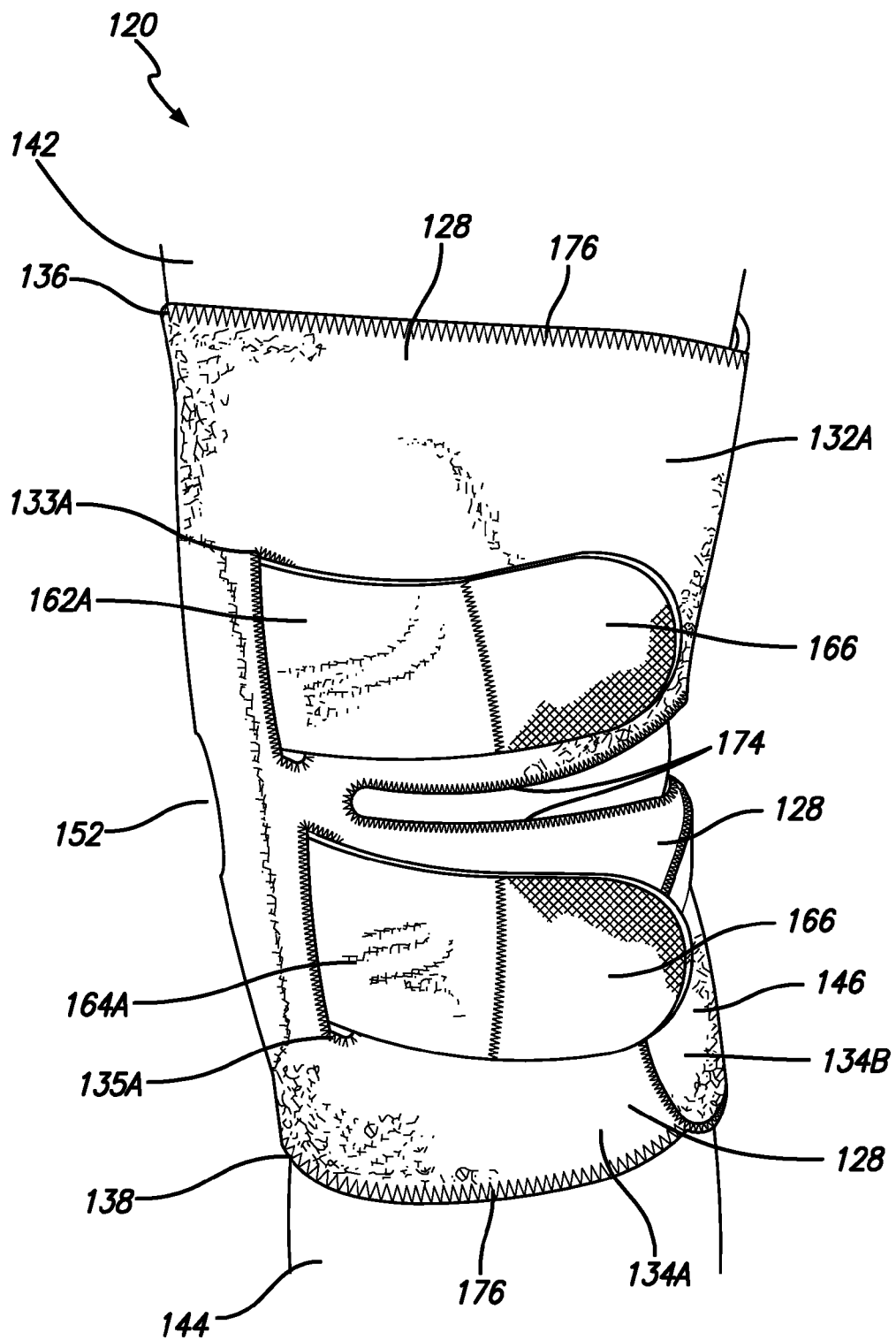
FIG. 4B is a side view of the knee brace of FIGS. 2A-2B, applied to the leg of a person with the base mounting straps fastened, and with the spider straps fastened as well.

As best shown in FIGS. 4A and 4B, when the base 122 of the knee brace 120 is applied to the leg of a person, the first upper mounting strap 132A overlaps the second upper mounting strap 132B at the rear of the leg, allowing the hook-type fastening tab 146 at the end of the first upper mounting strap 132A to adhere to the fabric bearing fiber loops 128 on the exterior surface of the second upper mounting strap 132B in order to fasten the knee brace 120 about the upper leg 142 of the wearer. Similarly, the first lower mounting strap 134A overlaps and adheres to the second lower mounting strap 134B at the rear of the leg in order to fasten the knee brace 120 about the lower leg 144 of the wearer.

The base 122 also preferably has a kneecap opening 152 to receive the patella (kneecap) when the brace is worn. The kneecap opening 152 can match the size of the kneecap, so that the kneecap of the wearer extends from the kneecap opening 152 when the brace 120 is worn, although this is not necessary. The kneecap opening 152 is preferably circular in shape, but this is not necessary and other shapes such as a diamond, oval, rectangle, or square shape may be used. In addition to providing direct patella stabilization, the kneecap opening 152 may help to locate the brace 120 with respect to the kneecap during application of the brace 120.

The base 122 may be formed to include a recess 174 between the upper mounting straps 132A, 132B and the lower mounting straps 134A, 134B, so that when the knee brace 120 is fitted upon the leg the gaps on each side form an opening at the rear of the knee, although this is not required. The recess 174 can help to avoid chafing, it can provide ventilation, and it can help avoid bunching or undue restriction of movement.

The base 122 is preferably formed, as shown in FIGS. 2A-2B, as a reclosable sleeve made from a sheet of elastic material that provides generalized support and compression to the knee area, along with therapeutic warming, but other materials may be used. The base 122 may also be formed, for example, as a tubular elastic sleeve shaped to fit snugly about the knee and adjacent leg portions. The base preferably includes edge binding 176, although none of these features are required.

As perhaps best shown in FIG. 2B which shows the interior surface 139 of the base 122, the knee brace 120 includes a spider member 124. The spider member 124 has a spider member central portion 154 extending vertically from an upper edge 156 to a lower edge 158, and has a mid-line axis 160 running vertically down the middle of the spider member central portion 154. The central portion 154 of the spider member 124 is permanently attached to the interior surface 139 of the base 122 by stitches 171 that extend along the mid-line axis 160 of the spider member central portion 54.

The spider member 124 includes a first upper tensioning strap 162A, a second upper tensioning strap 162B, a first lower tensioning strap 164A, and a second lower tensioning strap 164B extending from the central portion 154. Each of the tensioning straps 162A, 162B, 164A, 164B terminates in hook-type fastening tabs 166 suitable for detachable attachment to the fabric bearing fiber loops 128 on the exterior surface of the base 122 and sewn to the tensioning straps with stitches 168. The spider member 124 also has a kneecap opening 170 to receive the kneecap when the brace is worn.

While there are some similarities between the prior art knee brace 20 and a knee brace 120 according to the present invention, there are (without limitation) at least three important differences. First, the spider member 24 of the prior art knee brace 20 is fastened to the exterior surface 31 of the base 22. In contrast, the spider member 124 of the knee brace 120 according to the present invention is fastened to the interior surface 139 of the base 122.

Second, the spider member 24 of the prior art knee brace 20 is fastened to the base 22 by stitches 72 that extend around the periphery of the spider member central portion 54. In contrast, the spider member 124 of the knee brace 120 is fastened to the base 122 by stitches 171 that extend along the mid-line axis 160 of the spider member central portion 54.

Third, both the central portion 54 and the tensioning straps 62A, 62B, 64A, 64B of the spider member 24 of the prior art knee brace 20 are on the exterior surface 31 of the base 22 during normal use. In contrast, in the knee brace 120 the central portion 154 of the spider member 124 is on the interior surface 139 of the base 122, and the tensioning straps 162A, 162B, 164A, and 164B extend through apertures 133A, 133B, 135A, 135B to reach the exterior surface 131 of the base 122.

There are various possibilities with regard to alternative embodiments of a knee brace according to the invention.

Although in a preferred embodiment the knee brace includes a base which is formed as a reclosable sleeve made from a sheet of elastic material, this is not required. For example, the base may also be formed of a tubular elastic sleeve shaped to fit snugly about the knee and adjacent leg portions. The base does not need to include a kneecap opening, and the kneecap opening, if present, could have a variety of shapes, e.g. circular, square, rectangular, elliptical, diamond, trapezoidal, or any substantial equivalent. All such alternative embodiments will be referred to herein as a base.

Although in a preferred embodiment the lateral sides of the base each terminate in upper and lower fastening straps, with a side recess between the upper and lower fastening straps, this is not required. For example, the sides of the base, or portions thereof, could be straight.

Although in a preferred embodiment the base is detachably fastened about the leg of the wearer using hook and loop material of the type which adheres when pressed together, this is not required. For example, other fasteners such as buttons, clasps, buckles, pins, zippers, straps, buttons or other substantial equivalents may be substituted for the hook and loop type fastener material.

Although in a preferred embodiment, various components are permanently fastened together using stitches, this is not required. For example, other means such as glue, thermal bonding, or other substantial equivalents could be used.

One or more upright support members may be provided on one side, or on both sides, of the base of the knee brace, to provide support and protect the knee against abnormal motions, although this is not required. The upright support members may be formed, for example, by placing a resilient stay member in an elongated side pocket. The resilient stay members may be comprised of a flattened spiral core of stainless steel or other flexible material of conventional construction commonly used in various types of braces.

The elongate side pocket may be formed, for example, between vertical sewn seams that fix a side pocket cover strip to the base. The side pocket cover strip may be made of the same elastic sheet material as the base, although this is not necessary. Edge binding may be fastened to the edges of the side pocket cover strips, although this is not necessary.

The exact number, location, and construction of the upright support members may vary if provided. For example, there may be a single elongated side pocket forming only one upright support member, or there may be one or more elongated side pockets on each side of the knee with a resilient stay in each elongated side pocket. The elongated side pockets may be openable at one end to allow removal of the resilient stays, so that the brace may be washed or so that different resilient stays may be inserted to adjust the amount and type of support provided. The upright support members may include mechanical hinges, plastic rods, metal rods, narrow strips of reinforcing sheet material, or other substantial equivalents, or a combination of these various alternatives.

Advantageously, the external surface of the front of a knee brace according to the invention does not bear any structure, and can be smooth except for any stitches that secure the spider member to the inside of the base. The smooth external surface can be maintained, for example to provide an attractive and clean appearance that will not snag or obstruct motion during use. Alternatively other structures such as thick knee pads for use in contact sports like football or in trades like concrete or floor tile work, or slippery material for use in sports like volleyball, could be positioned on the external surface for particular applications.

It is understood that the invention is not confined to the embodiments set forth herein as illustrative, but embraces all such forms thereof that come within the scope of the following claims.

What is claimed is:

1. A knee brace, comprising:
  a) a base wearable in snug covering relationship to portions of a knee and adjacent portions of a leg of a person, the base having an exterior surface and an interior surface when worn; and
  (b) a spider member having a first upper tensioning strap, a second upper tensioning strap, a first lower tensioning strap, and a second lower tensioning strap,
  wherein the spider member is positioned between the base and the leg of the person when worn;
  wherein the base includes a first upper aperture, a second upper aperture, a first lower aperture, and a second lower aperture;
  and wherein the first upper tensioning strap extends through the first upper aperture, wherein the second upper tensioning strap extends through the second upper aperture, wherein the first lower tensioning strap extends through the first lower aperture, and wherein the second lower tensioning strap extends through the second lower aperture when the brace is worn.

2. he knee brace of claim 1 wherein at least a portion of the exterior surface of the base bears loop-type material, and
  wherein each of the first upper tensioning strap, the second upper tensioning strap, the first lower tensioning strap, and the second lower tensioning strap has a free end bearing a hook-type material,
  whereby the free ends of the tensioning straps may be detachably attached to the exterior surface of the base.

3. The knee brace of claim 1 wherein the base has a base central portion mid-line axis, wherein the spider member has a spider member central portion mid-line axis, and wherein the spider member is permanently fastened to the base by a plurality of stitches through at least a portion of the base central portion mid-line axis and through at least a portion of the spider member central portion mid-line axis.

4. The knee brace of claim 3 wherein the spider member is not otherwise permanently attached to the base.

5. The knee brace of claim 1 wherein the spider member is permanently fastened to the interior surface of the base.

* * * * *